United States Patent
Indani et al.

(10) Patent No.: US 11,756,051 B2
(45) Date of Patent: Sep. 12, 2023

(54) SYSTEM AND METHOD FOR CUSTOM-MADE MEDICAL DEVICES LIFE CYCLE MANAGEMENT

(71) Applicant: Tata Consultancy Services Limited, Mumbai (IN)

(72) Inventors: Ashish Omprakash Indani, Mumbai (IN); Saurabh Das, Mumbai (IN); Devraj Goulikar, Mumbai (IN); Biswamohan Routray, Mumbai (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 380 days.

(21) Appl. No.: 17/159,368

(22) Filed: Jan. 27, 2021

(65) Prior Publication Data

US 2021/0272134 A1   Sep. 2, 2021

(30) Foreign Application Priority Data

Jan. 29, 2020   (IN) .............................. 202021004022

(51) Int. Cl.
*G16H 10/40* (2018.01)
*G06Q 30/018* (2023.01)
(Continued)

(52) U.S. Cl.
CPC ............ *G06Q 30/0185* (2013.01); *A61L 2/24* (2013.01); *A61L 2/28* (2013.01); *B33Y 50/00* (2014.12);
(Continued)

(58) Field of Classification Search
CPC .. G06Q 30/0185; G06Q 10/101; G06Q 50/04; G06Q 10/06395; B33Y 50/00;
(Continued)

(56) References Cited

U.S. PATENT DOCUMENTS

| | | | |
|---|---|---|---|
| 8,234,128 B2 | 7/2012 | Martucci et al. | |
| 2014/0263674 A1 * | 9/2014 | Cerveny | G06K 19/06037 |
| | | | 235/494 |

(Continued)

FOREIGN PATENT DOCUMENTS

| | | | | |
|---|---|---|---|---|
| CN | 108540553 A | | 9/2018 | |
| EP | 3859740 A1 * | 8/2021 | ............... A61L 2/24 |

(Continued)

*Primary Examiner* — Michael Tomaszewski
(74) *Attorney, Agent, or Firm* — Finnegan, Henderson, Farabow, Garrett & Dunner LLP (57) ABSTRACT

This disclosure relates to a system and method for custom made medical devices life cycle management, the life cycle management of the medical devices include tracking of material and procedure to be used in additive manufacturing of the medical device and analyzing design risk as per the raw material and the design specification. Further, it includes to identify potential hazards based upon the materials, their interactions and effect on process to be followed. An artificial intelligence (AI) enabled model is trained with one or more sample datasets pertaining to a plurality of materials to be used in the additive manufacturing to audit design, to determine materials to be used, and to generate a unique code to be used to label the manufactured medical device. A smart contract of blockchain is configured to record received input and update with new points for regulatory compliance.

15 Claims, 3 Drawing Sheets

(51) Int. Cl.
| | |
|---|---|
| *B33Y 50/00* | (2015.01) |
| *B33Y 80/00* | (2015.01) |
| *G16H 10/60* | (2018.01) |
| *G16H 40/40* | (2018.01) |
| *G06F 16/27* | (2019.01) |
| *G06N 20/00* | (2019.01) |
| *G16Y 10/25* | (2020.01) |
| *G16Y 10/60* | (2020.01) |
| *G06F 30/27* | (2020.01) |
| *G16Y 40/20* | (2020.01) |
| *A61L 2/24* | (2006.01) |
| *A61L 2/28* | (2006.01) |
| *G06Q 10/101* | (2023.01) |
| *G06Q 50/04* | (2012.01) |
| *G16H 40/20* | (2018.01) |
| *G06Q 10/0639* | (2023.01) |

(52) U.S. Cl.
CPC .............. *B33Y 80/00* (2014.12); *G06F 16/27* (2019.01); *G06F 30/27* (2020.01); *G06N 20/00* (2019.01); *G06Q 10/101* (2013.01); *G06Q 50/04* (2013.01); *G16H 10/40* (2018.01); *G16H 10/60* (2018.01); *G16H 40/40* (2018.01); *G16Y 10/25* (2020.01); *G16Y 10/60* (2020.01); *G16Y 40/20* (2020.01); *A61L 2202/24* (2013.01); *G06Q 10/06395* (2013.01); *G16H 40/20* (2018.01)

(58) Field of Classification Search
CPC ........ B33Y 80/00; G16H 10/40; G16H 10/60; G16H 40/40; G16H 40/20; G06F 16/27; G06F 30/27; G06N 20/00; G16Y 10/25; G16Y 10/60; G16Y 40/20; A61L 2/24; A61L 2202/24; A61L 2/28
USPC ......................................................... 705/2–3
See application file for complete search history.

(56) References Cited

U.S. PATENT DOCUMENTS

| | | | |
|---|---|---|---|
| 2016/0085922 A1* | 3/2016 | Sweeney | A61B 90/90 705/2 |
| 2018/0096175 A1* | 4/2018 | Schmeling | G06F 1/3206 |
| 2019/0180291 A1* | 6/2019 | Schmeling | G16H 20/10 |

FOREIGN PATENT DOCUMENTS

| | | | |
|---|---|---|---|
| WO | WO-2018069736 A1 * | 4/2018 | ............ A61B 34/10 |
| WO | WO 2018/232510 A1 | 12/2018 | |

* cited by examiner

SYSTEM AND METHOD FOR CUSTOM-MADE MEDICAL DEVICES LIFE CYCLE MANAGEMENT

CROSS-REFERENCE TO RELATED APPLICATIONS AND PRIORITY

This U.S. patent application claims priority under 35 U.S.C. § 119 to India Application No. 202021004022, filed on Jan. 29, 2020. The entire content of the abovementioned application is incorporated herein by reference.

TECHNICAL FIELD

The disclosure herein generally relates to a field of medical device life cycle management and, more particularly, a system and method for custom-made medical devices life cycle management.

BACKGROUND

Additive manufacturing or 3D printing of medical devices has set a new miles-stone in the personalized medicine. The major approach change is about no requirement for any additional equipment or manufacturing set-up. Its flexibility is benevolent for designers who can make devices with complex internal structures or implement design changes at an ease. The 3D printing technique is majorly used in manufacturing patient-specific or personalized medical devices like implants or external prostheses. These devices are made to fit or mimic a person's anatomy even in extremely complex structures. Additionally, the 3D printing technique is uses for manufacturing instruments or equipment. There are sustained efforts to identify the opportunity for development of live organs using 3D printing technology.

While the 3D printing technology is broadening its horizons, several challenges in managing ethics and regulations of the devices have started popping up. All the regulations control all the medical devices at the point of manufacturing and not at the point of use or sale. Hence, the hospital printed medical devices was never a consideration of most of the regulations.

SUMMARY

Embodiments of the present disclosure provides technological improvements as solutions to one or more of the abovementioned technical problems recognized by the inventors in conventional systems.

In one aspect, a processor-implemented method to a custom-made medical device life cycle management. Wherein, the life cycle management of the medical devices include tracking of material and procedure to be used in additive manufacturing of the medical device and analyzing design risk as per the raw material and a design specification. Further, it includes to identify potential hazards based upon the materials, their interactions and effect on process to be followed.

The method comprises one or more steps as follows. Herein, training an artificial intelligence (AI) enabled model with one or more sample datasets pertaining to a plurality of materials to be used in the additive manufacturing, receiving a patient health record, a design information of a medical device, and at least one image of each of a plurality of materials to be used in an additive manufacturing of the medical device. Further, the received design of the medical device is audited using the trained AI enabled model and a smart contract of the blockchain. It would be appreciated that the smart contract of the blockchain comprises one or more regulation parameters to be followed in manufacturing the custom-made medical device using the additive manufacturing.

Further, one or more characteristics of each of the plurality of materials of the audited design of the medical device are determined using the trained AI enabled model. The determined one or more characteristics are updated in the smart contract of the blockchain. The manufactured medical device is analyzed based on the trained AI enabled model and the updated smart contract of the blockchain, wherein the smart contract is also updated based on consensus achieved among a plurality of stakeholders. The analyzed medical device is labelled with a unique code based on one or more information received from an internet of things (IoT) devices and, the trained AI enabled device. It would be appreciated that the unique code comprises one or more information of the medical device.

In another aspect, a system is configured for a custom-made medical device life cycle management. Wherein, the life cycle management of the custom-made medical device includes tracking of material and procedure to be used in additive manufacturing of the medical device and analyzing design risk as per the raw material and the design specification. Further, the system is configured to identify potential hazards based upon the materials, their interactions and effect on process to be followed.

The system comprising at least one user interface, at least one memory storing a plurality of instructions and one or more hardware is processors communicatively coupled with at least one memory. The one or more hardware processors are configured to execute one or more modules comprises of a training module, a receiving module, an auditing module, a determining module, an analyzing module, a labeling module, and a natural language processing (NLP) module.

The training module is configured to train an artificial intelligence (AI) enabled model with one or more sample datasets pertaining to a plurality of materials to be used in the additive manufacturing, and a plurality of design information of a plurality of medical devices. The receiving module of the system is configured to receive a patient health record, a design information of a medical device, and at least one image of each of a plurality of materials to be used in an additive manufacturing of the medical device. The auditing module of the system is configured to audit the received at least one design of the medical device using the trained AI enabled model and a smart contract of the blockchain. It is to be noted that the smart contract of the blockchain comprises one or more regulation parameters to be followed in manufacturing the custom-made medical device using the additive manufacturing.

Further, the determining module of the system is configured to determine one or more characteristics of each of the plurality of materials of the audited design of the medical device using the trained AI enabled model. Herein, the determined one or more characteristics are updated in the smart contract of the blockchain. The analyzing module of the system is configured to analyze the manufactured medical device based on the AI enabled model and the updated smart contract of the blockchain. It would be appreciated that consensus is achieved among a plurality of stakeholders through the smart contract of the blockchain. The labeling module of the system is configured to label the analyzed medical device with a unique code based on one or more information received from an Internet of things (IoT)

devices and the AI enabled model. The natural language processing module (118) of the system is configured to utilize the updated smart contract of the blockchain to process the compliance record, and the unique code labelled on the manufactured device to prepare a dossier for regulatory compliance.

In yet another aspect, a non-transitory computer readable medium storing one or more instructions which when executed by a processor on a system cause the processor to perform method is provided.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes, which may be substantially represented in computer readable medium and so executed by a computer or processor, whether or not such computer or processor is explicitly shown.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The embodiments herein provide a method and a system for a custom-made medical device life cycle management. Wherein, the life cycle management of the medical devices include tracking of material and procedure to be used in additive manufacturing of the medical device and analyzing design risk as per the raw material and the design specification. Further, the system is configured to identify potential hazards based upon the materials, their interactions and effect on process to be followed.

Figure 1:
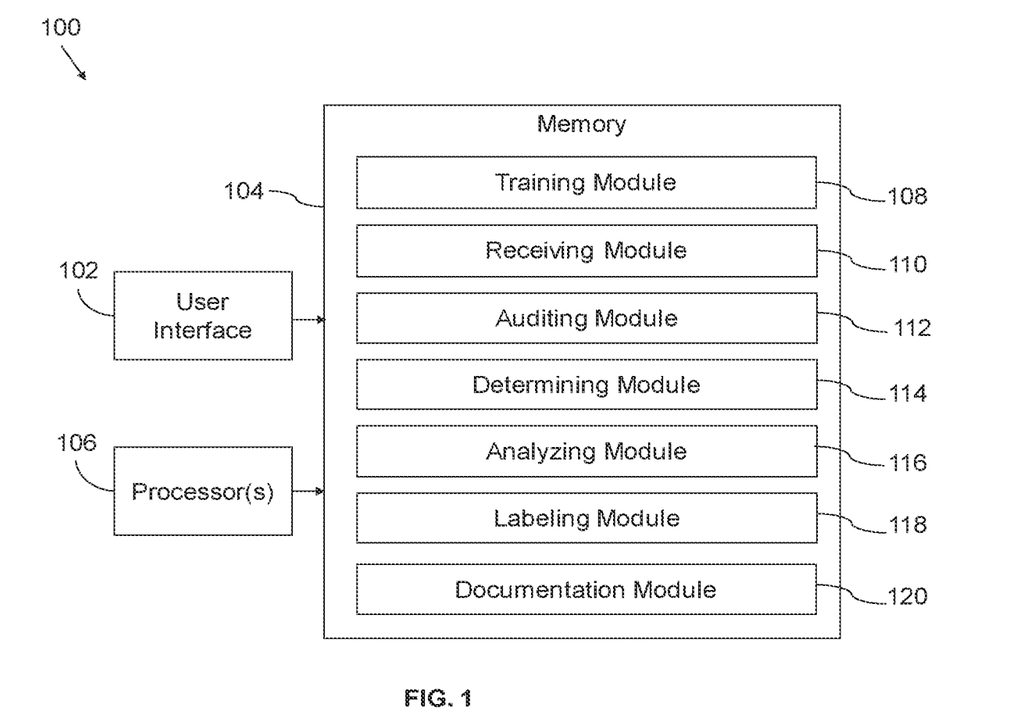
FIG. 1 illustrates a system for a custom-made medical devices life cycle management, in accordance with some embodiments of the present disclosure.
Figure 2:
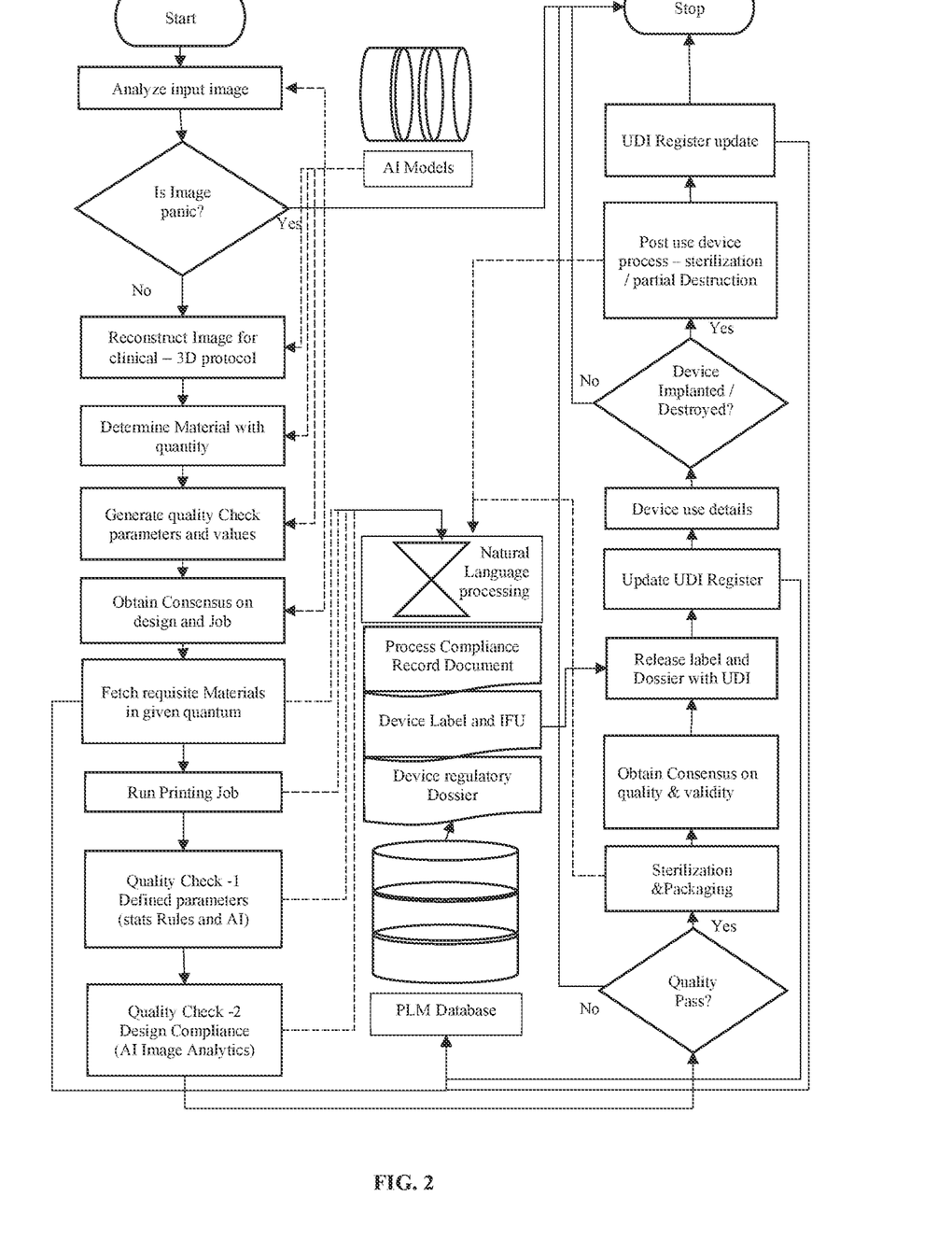
FIG. 2 is a functional block diagram of the system for a custom-made medical devices life cycle management, in accordance with some embodiments of the present disclosure.
Figure 3:
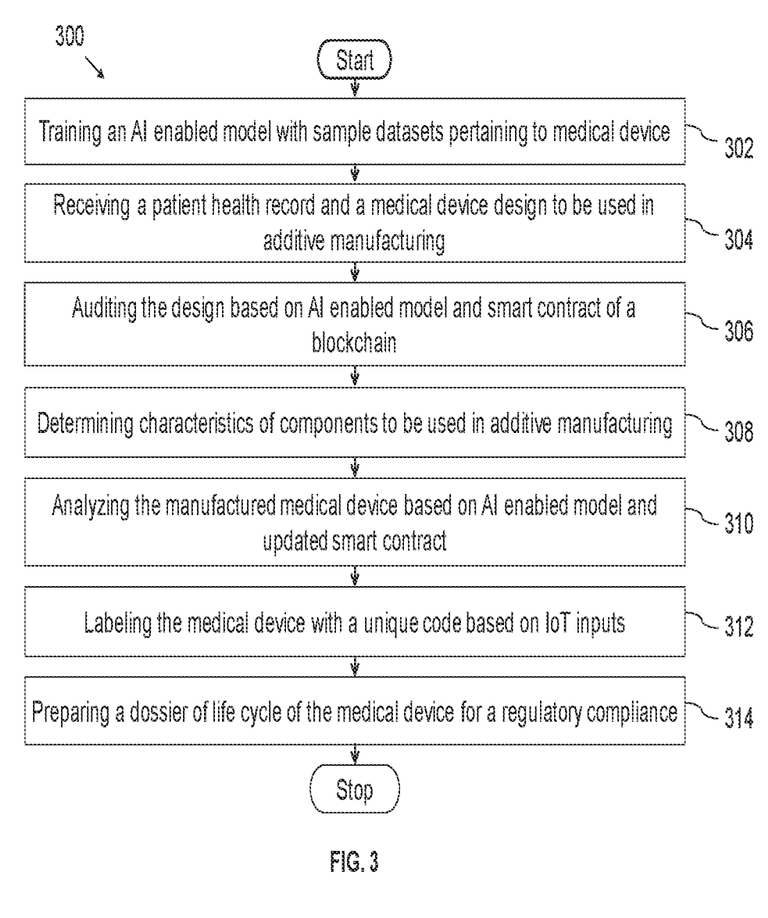
FIG. 3 is a flow diagram to illustrate a method for a custom-made medical device life cycle management, in accordance with some embodiments of the present disclosure.

Referring now to the drawings, and more particularly to FIG. 1 through FIG. 3, where similar reference characters denote corresponding features consistently throughout the figures, there are shown preferred embodiments and these embodiments are described in the context of the following exemplary system and/or method.

FIG. 1 illustrates a system (100) for a custom-made medical device life cycle management. In the preferred embodiment, the system (100) comprises at least one user interface (102), at least one memory (104) with a plurality of instructions and one or more hardware processors (106) which are communicatively coupled with the at least one memory (104) to execute modules therein. The system (100) is configured to analyze design risks as per the raw material and the design specification. These risks include injury, uneven strength leading to breaking, or potential non-performance of the medical device for its intended purpose.

Further, the system (100) is configured to identify potential hazards based upon the materials, their interactions and effect of process to be followed. The system (100) is able to suggest ending of completion of manufacturing process including sterilization and sterilization validation. The system (100) has communication ability to communicate with a supplier of raw materials, regulation or central regulatory registers, medical records and the supplier of the 3D printed medical devices. The user interface (102) of the system (100) allows easy retrieval of the data by simple or semantic or customized or any form of queries incase if the data retrieval is required.

The hardware processor (106) may be implemented as one or more microprocessors, microcomputers, microcontrollers, digital signal processors, central processing units, state machines, logic circuitries, and/or any devices that manipulate signals based on operational instructions. Among other capabilities, the hardware processor (106) is configured to fetch and execute computer-readable instructions stored in the memory (104). Further, the system comprises a training module (108), a receiving module (110), an auditing module (112), a determining module (114), an analyzing module (116), a labeling module (118), documentation module (120).

In the preferred embodiment of the disclosure, the training module (108) of the system (100) is configured to train an artificial is intelligence (AI) enabled model with one or more sample datasets pertaining to a plurality of materials to be used in the additive manufacturing, and a plurality of design information of a plurality of medical devices.

In the preferred embodiment of the disclosure, the receiving module (110) of the system (100) is configured to receive a patient health record, a design information of a medical device, and at least one image of each of a plurality of materials to be used in an additive manufacturing of the medical device. Herein, the plurality of materials includes chemicals, and animal and human tissues. The received at least one image of each of a plurality of materials are input to the AI enabled model to analyze various dimensions based on one or more predefined parameters. Herein, the plurality of materials is either in the basic form or customized form can be used alone or in combination with other materials.

In the preferred embodiment of the disclosure, the auditing module (112) of the system (100) is configured to audit the received at least one design of the medical device using the trained AI enabled model and a smart contract of the blockchain. The smart contract of the blockchain comprises one or more regulation parameters to be followed in manufacturing the medical device using the additive manufacturing. The smart contract includes an entire record of quality check of each medical device along with signature of an authorized person for the same. Further, the smart contract is updated based on a finality consensus among the stakeholders. Herein, the stakeholders include an owner of the design, an image creator or a radiologist, a treating doctor, a supplier of raw materials etc.

In the preferred embodiment of the disclosure, the determining module (114) of the system (100) is configured to determine one or more characteristics of each of the plurality of materials of the audited design of the medical device using the trained AI enabled model, wherein the determined one or more characteristics are recorded in the smart contract of the blockchain.

In the preferred embodiment of the disclosure, the analyzing module (116) of the system (100) is configured to analyze the manufactured medical device based on the trained AI enabled model and the smart contract of the blockchain, wherein a consensus is achieved among a plurality of stakeholders through the smart contract of the blockchain. It would be appreciated that the smart contract restricts unauthorized reprinting of the medical devices based on the consensus achieved. There are limitations to print the medical device and the smart contract triggers alerts for the plurality of stakeholders, when a panic activity is noted at the analyzing module (114) of the system (100).

In the preferred embodiment of the disclosure, the labeling module (118) of the system (100) is configured to label the analyzed medical device with a unique code based on one or more information received from an Internet of things (IoT) devices, the pre-trained artificial intelligence model and updated smart contract of the blockchain. It is to be noted that the unique code comprises patient detail, and design information of a medical device.

The labelled medical devices are packaged and arranged into smart trays for which a batch number and a serial number is predefined at the quality check level. Then the labelled devices are taken to sterilization. The record of sterilization of each batch is generated through IoT devices and the record is updated on the smart contract of the blockchain.

In another embodiment, the documentation module (120) of the system (100) is configured to utilize the smart contract of the blockchain to process the compliance record, and the unique code labelled on the manufactured device to prepare a dossier for regulatory compliance.

It would be appreciated that the labelled medical device is tracked and the device that is disposable or partially disposable, then gets disposed through an IoT based shredder. Smart sensors of the IoT devices are used for a smart packaging and the smart contract is updated with device life cycle. Further, the medical device uses in-patient or healthy user is tracked through smart sensors of clinical or pharmacy arrangements. Furthermore, as there are entire set of documentation available even for the medical device, the custom-made medical device can be treated as a traditional made device for regulatory and reimbursement purposes to the regulators and insurance companies.

Referring FIG. 2, a functional flow chart illustrating a point of care additive manufacturing of custom-made medical devices and the system to track the medical device's used materials and procedures. An artificial intelligence (AI) enabled model is trained with one or more sample datasets pertaining to a plurality of materials to be used in the additive manufacturing, and a plurality of design information of a plurality of medical devices. A patient health record, a design information of a medical device, and at least one image of each of a plurality of materials to be used in an additive manufacturing of the medical device. The received design of the medical device is audited using the trained AI enabled model and a smart contract of the blockchain. It is to be noted that the smart contract of the blockchain comprises one or more regulation parameters to be followed in manufacturing the custom-made medical device using the additive manufacturing. Characteristics of received materials of the audited design of the medical device is determined and the smart contract is updated accordingly. The manufactured medical device is analyzed based on the AI enabled model and the updated smart contract of the blockchain. It would be appreciated that consensus is achieved among a plurality of stakeholders through the smart contract of the blockchain. The medical devices are labeled with a unique code based on one or more information received from an internet of things (IoT) devices and the AI enabled model, A natural language processing is used to utilize the updated smart contract of the blockchain to process the compliance record, and the unique code labelled on the manufactured device to prepare a dossier for regulatory compliance.

Referring FIG. 3, a processor-implemented method (300) for a custom-made medical device life cycle management. The method comprises one or more steps as follows.

Initially, at the step (302), training an artificial intelligence (AI) enabled model at the training module (108) of the system (100) with one or more sample datasets pertaining to a plurality of materials to be used in the additive manufacturing, and a plurality of design information of a plurality of medical devices.

In the preferred embodiment of the disclosure, at the next step (304), receiving a patient health record, a design information of a medical device, and at least one image of each of a plurality of component to be used in an additive manufacturing of the medical device at the receiving module (110) of the system (100).

In the preferred embodiment of the disclosure, at the next step (306), auditing, the received at least one design of the medical device at the auditing module (112) of the system (100) using the trained AI enabled model and a smart contract of the blockchain. The smart contract comprises one or more regulation parameters to be followed in manufacturing the medical device using the additive manufacturing.

In the preferred embodiment of the disclosure, at the next step (308), determining one or more characteristics of each of the plurality of materials of the audited design of the medical device at the determining module (114) of the system (100) using the trained AI enabled model. The determined one or more characteristics are updated in the smart contract of the blockchain.

In the preferred embodiment of the disclosure, at the next step (310), analyzing the manufactured medical device at the analyzing module (116) of the system (100) based on the trained AI enabled model and the updated smart contract of the blockchain. It is to be noted that a consensus is achieved among a predefined plurality of stakeholders through the smart contract of the blockchain and the smart contract is updated with the recommendations from the one or more predefined stakeholders.

In the preferred embodiment of the disclosure, at the next step (312), labelling the analyzed medical device with a unique code at the labeling module (118) of the system (100) based on one or more information received from an internet of things (IoT) devices and the trained AI enabled model. Herein, the unique code comprises one or more information of the medical device.

In the preferred embodiment of the disclosure, at the next step (314), preparing a dossier at the documentation module (120) of the system (100) for regulatory compliance of the manufactured medical device using the updated smart contract of the blockchain and the natural language processing of the system (100).

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem associated with 3D printed medical device life cycle management. In hospitals, 3D printed medical devices and custom-made devices especially from the human tissues are intended to be manufactured at the point of care yet, treating doctors or the institute cannot be called manufacturer and do not fall under jurisdiction of medical device regulators in respective countries. Therefore, there are issues like lacking traceability of the medical device and its materials with printed at the point of care, lacking ownership for reporting, and unclear regulations about in-hospital 3D printed medical devices.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device, which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing materials located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various materials described herein may be implemented in other materials or combinations of other materials. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development would change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method, comprising:
   training, via one or more hardware processors, an artificial intelligence (AI) enabled model with one or more sample datasets pertaining to:
      a plurality of materials to be used in an additive manufacturing, and
      a plurality of design information of a plurality of medical devices manufactured via the additive manufacturing;
   receiving, via one or more hardware processors, a patient health record, a design information of a medical device, and at least one image of each of the plurality of materials to be used in the additive manufacturing of the medical device;
   auditing, via one or more hardware processors, the received design information of the medical device using the trained AI enabled model and a smart contract of a blockchain, wherein the smart contract comprises one or more regulation parameters to be followed in manufacturing of the medical device using the additive manufacturing;
   determining, via one or more hardware processors, one or more characteristics of each of the plurality of materials of the audited design of the medical device using the trained AI enabled model, wherein the determined one or more characteristics are updated in the smart contract of the blockchain;
   analyzing, via one or more hardware processors, the manufactured medical device based on the trained AI enabled model and a consensus is achieved among a plurality of stakeholders through the smart contract of the blockchain, wherein the analyzed medical device is tracked using one or more Internet of things (IoT) devices, wherein the trained AI enabled model analyzes design risks based on the audited design and the one or more characteristics of plurality of materials used in the additive manufacturing of the medical device, and wherein the design risks include injury, uneven strength leading to breaking, and potential non-performance of the medical device for intended purpose; and labelling, via one or more hardware processors, the analyzed medical device with a unique code based on one or more information received from the one or more internet of things (IoT) devices, the trained AI enabled model, and the updated smart contract of the blockchain, wherein the unique code comprises one or more information of the medical device, wherein the smart contract restricts unauthorized printing of the plurality of medical devices based on the consensus achieved, and wherein the labelled medical device is tracked and the labelled medical device that is disposable or partially disposable are disposed through at least one of the one or more IoT devices.

2. The processor-implemented method of claim 1, wherein the plurality of materials to be used in the additive manufacturing include chemicals, and animal and human tissues.

3. The processor-implemented method of claim 1, wherein the unique code comprises patient detail, the design information of the medical device, origin of the plurality of materials, laboratory test codes, and date and time of manufacturing and to be best to use.

4. The processor-implemented method of claim 1, wherein the AI enabled model is trained to identify potential hazards based upon the plurality of materials, and effect of process to be followed.

5. The processor-implemented method of claim 1, wherein the AI enabled model is trained to suggest at the end of completion of manufacturing process including sterilization and sterilization validation.

6. The processor-implemented method of claim 1, wherein end-to-end life cycle of the medical device is updated with the smart contract of the blockchain.

7. The processor-implemented method of claim 1, wherein a dossier for a regulatory compliance is prepared to utilize the smart contract of the blockchain to process the compliance record, and the unique code labelled on the manufactured medical device.

8. The system comprising:
at least one user interface;
at least one memory storing a plurality of instructions;
one or more hardware processors communicatively coupled with at least one memory, wherein one or more hardware processors are configured to execute one or more modules;
a training module configured to train an artificial intelligence (AI) enabled model with one or more sample datasets pertaining to a plurality of materials to be used in an additive manufacturing, and a plurality of design information of a plurality of medical devices manufactured via the additive manufacturing;
a receiving module configured to receive a patient health record, a design information of a medical device, and at least one image of each of the plurality of materials to be used in the additive manufacturing of the medical device;

an auditing module configured to audit the received design information of the medical device using the trained AI enabled model and a smart contract of a blockchain, wherein the smart contract comprises one or more regulation parameters to be followed in manufacturing the medical device using the additive manufacturing;

a determining module configured to determine one or more characteristics of each of the plurality of materials of the audited design of the medical device using the trained AI enabled model, wherein the determined one or more characteristics are updated in the smart contract of the blockchain;

an analyzing module configured to analyze the manufactured medical device based on the trained AI enabled model and a consensus is achieved among a plurality of stakeholders through the smart contract of the blockchain, wherein the analyzed medical device is tracked using one or more Internet of things (IoT) devices, wherein the trained AI enabled model is configured to analyze design risks based on the audited design and the one or more characteristics of plurality of materials used in the additive manufacturing of the medical device, and wherein the design risks include injury, uneven strength leading to breaking, and potential non-performance of the medical device for intended purpose; and a labeling module configured to label the analyzed medical device with a unique code based on one or more information received from the one or more internet of things (IoT) devices, the trained AI enabled model, and the updated smart contract of the blockchain, wherein the unique code comprises one or more information of the medical device, wherein the smart contract restricts unauthorized printing of the plurality of medical devices based on the consensus achieved, and wherein the labelled medical device is tracked and the labelled medical device that is disposable or partially disposable are disposed through at least one of the one or more IoT devices.

9. The system of claim 8, further comprising:
a documentation module configured to utilize the smart contract of the blockchain to process the compliance record, and the unique code labelled on the manufactured device to prepare a dossier for regulatory compliance.

10. The system of claim 8, wherein the plurality of materials to be used in the additive manufacturing include chemicals, and animal and human tissues.

11. The system of claim 8, wherein the unique code comprises patient detail, the design information of the medical device, origin of the plurality of materials, laboratory test codes, and date and time of manufacturing and to be best to use.

12. The system of claim 8, wherein the AI enabled model is trained to identify potential hazards based upon the plurality of materials, and effect of process to be followed.

13. The system of claim 8, wherein the AI enabled model is trained to suggest at the end of completion of manufacturing process including sterilization and sterilization validation.

14. The system of claim 8, wherein end-to-end life cycle of the medical device is updated with the smart contract of the blockchain.

15. A non-transitory computer readable medium storing one or more instructions which when executed by a processor on a system, cause the processor to perform method comprising:

training an artificial intelligence (AI) enabled model with one or more sample datasets pertaining to:
a plurality of materials to be used in an additive manufacturing, and
a plurality of design information of a plurality of medical devices manufactured via the additive manufacturing;
receiving a patient health record, a design information of a medical device, and at least one image of each of the plurality of materials to be used in the additive manufacturing of the medical device;
auditing the received design information of the medical device using the trained AI enabled model and a smart contract of a blockchain, wherein the smart contract comprises one or more regulation parameters to be followed in manufacturing of the medical device using the additive manufacturing;
determining one or more characteristics of each of the plurality of materials of the audited design of the medical device using the trained AI enabled model, wherein the determined one or more characteristics are updated in the smart contract of the blockchain;
analyzing the manufactured medical device based on the trained AI enabled model and a consensus is achieved among a plurality of stakeholders through the smart contract of the blockchain, wherein the analyzed medical device is tracked using one or more Internet of things (IoT) devices, wherein the trained AI enabled model analyzes design risks based on the audited design and the one or more characteristics of plurality of materials used in the additive manufacturing of the medical device, and wherein the design risks include injury, uneven strength leading to breaking, and potential non-performance of the medical device for intended purpose; and
labelling the analyzed medical device with a unique code based on one or more information received from the one or more internet of things (IoT) devices, the trained AI enabled model, and the updated smart contract of the blockchain, wherein the unique code comprises one or more information of the medical device, wherein the smart contract restricts unauthorized printing of the plurality of medical devices based on the consensus achieved, and wherein the labelled medical device is tracked and the labelled medical device that is disposable or partially disposable are disposed through at least one of the one or more IoT devices.

* * * * *